United States Patent [19]
Makriyannis et al.

[11] Patent Number: 5,872,148
[45] Date of Patent: Feb. 16, 1999

[54] COMPOSITIONS USEFUL AS A CANNABINOID RECEPTOR PROBE

[75] Inventors: Alexandros Makriyannis, Ashford, Conn.; Yan Guo, Clinton, N.J.; Vasiliki Abadji, Boston, Mass.

[73] Assignee: University of Connecticut, Storrs, Conn.

[21] Appl. No.: 512,864

[22] Filed: Aug. 8, 1995

Related U.S. Application Data

[62] Division of Ser. No. 103,883, Aug. 6, 1993, Pat. No. 5,440,052.

[51] Int. Cl.$^6$ .......................... A61K 31/35; C07D 311/80
[52] U.S. Cl. ............................................ 514/454; 549/390
[58] Field of Search ............................. 549/390; 514/454

[56] References Cited

U.S. PATENT DOCUMENTS 3,897,306  7/1975  Vidic et al. .

OTHER PUBLICATIONS

Reggio, P.H. et al., "Characterization of a Region of Steric Interference at the Cannabinoid Receptor Using the Active Analog Approach", *J. Med. Chem.* United States, 36(12):1761–1771, (Jun. 11, 1993).

Gold, L.H. et al., "A Comparison of the Discriminative Stimulus Properties of $\Delta^9$–Tetrahydrocannabinol and CP 55,940 in Rats and Rhesus Monkeys", *J. Pharmacol. Exp. Ther.*, 262(2):479–486, (Aug. 1992).

Charalambous, A. et al., "Pharmacological Evaluation of Halogenated $\Delta^8$–THC Analogs", *Pharmacol. Biochem. Behav.*, 40(3):509–512 (Nov. 1991).

Martin, B.R. et al., "Behavioral, Biochemical, and Molecular Modeling Evaluations of Cannabinoid Analogs", *Pharmacol. Biochem. Behav.*, 40(3):471–478 (Nov. 1991).

Compton, D.R. et al., "Synthesis and Pharmacological Evaluation of Ether and Related Analogues of $\Delta^8$–, $\Delta^9$–, and $\Delta^{9,11}$–Tetrahydrocannabinol", *J. Med. Chem.*, 34(11):3310–3316 (Nov. 1991).

Burstein, S.H. et al., "Detection of Cannabinoid Receptors by Photoaffinity Labelling", *Biochem. Biophys. Res. Commun.*, 176(1):492–497 (Apr. 15, 1991).

Howlett, A.C. et al., "Stereochemical Effects of 11–OH–$\Delta^8$–Tetrahydrocannabinol–Dimethylheptyl to Inhibit Adenylate Cyclase and Bind to the Cannabinoid Receptor", *Neuropharmacology*, 29(2):161–165 (Feb. 1990).

Nye, J.S. et al., "High–Affinity Cannabinoid Binding Sites in Brain Membranes Labeled with [$^3$H]–5'–Trimethylammonium $\Delta^8$–Tetrahydrocannabinol", *J. Pharmacol. Exp. Ther.*, 234(3):784–791 (1985).

Charalambous, A., et al., "5'–Azido–$\Delta^8$–THC: A Novel Photoaffinity Label for the Cannabinoid Receptor", *J. Med. Chem.*, 35:3076–3079, (1992).

*The Merck Index*, Eleventh Edition, Entry #9142, (1989).

*Primary Examiner*—Johann Richter
*Assistant Examiner*—Joseph Murray
*Attorney, Agent, or Firm*—Hamilton,Brook,Smith & Reynolds, P.C.

[57] ABSTRACT

A composition of matter, comprising a cannabinol compound having the structure

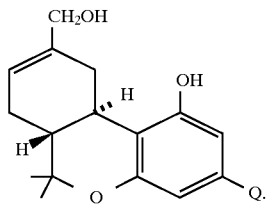

wherein,
Q is —C(R$^1$)(Y$^1$)—(CH$_2$)$_n$—Z$^1$; R$^1$ is —H or —CH$_3$;
Y$^1$ is —CH$_3$ or Y$^2$; Y$^2$ is —N$_3$ or —NCS; n is 4 or 6;
Z$^1$ is —H, when Y$^1$ is Y$^2$, or is Z$^2$, when Y$^1$ is —CH$_3$; and
Z$^2$ is —N$_3$ or —NCS.

This composition has good binding affinity to the cannabinoid receptor and therefore, is useful as a receptor probe.

4 Claims, 3 Drawing Sheets

COMPOSITIONS USEFUL AS A CANNABINOID RECEPTOR PROBE

RELATED APPLICATION

This application is a division of application Ser. No. 08/103,883 filed Aug. 6, 1993, now U.S. Pat. No. 5,440,052.

BACKGROUND OF THE INVENTION

Various preparations of the plant *Cannabis sativa* have been used since ancient times for their behavioral and pharmacological properties. R. Mechoulam, *The Pharmohistory of Cannabis Sativa*, 1–19 (1986). More recently, it has been demonstrated that the active plant constituents, known as cannabinoids, produce a variety of effects including bronchodilation, increased heart rate, reduced intraocular pressure, analgesia, antiemesis, alteration in body temperature, as well as anticonvulsant and psychotropic activities. (W. L. Dewey, *Cannabinoid Pharmacology, Pharmacol. Rev.*, 38:45 (1986)).

Recent evidence supports the hypothesis that cannabinoids also produce some of their effects by interacting with specific protein sites in synaptosomal preparations and mammalian brains. (W. A. Devane et al., "Determination and Characterization of a Cannabinoid Receptor in Rat Brain", *Mol. Pharmacol.*, 34:605–613 (1988); M. Herkenham et al., "Cannabinoid Receptor Localization in Brain", *Proc. Natl. Acad. Sci. USA*, 87:1932–1936 (1990)). For example, a cannabinoid receptor was shown to be more responsive to the psychoactive cannabinoids than the non-psychoactive derivatives. (A. C. Howlett, "Cannabinoid Inhibition of Adenylate Cyclase Relative Activity of Constituents and Metabolites of Marihuana", *Neuropharmacology*, 26:507–512 (1987)). More recently, the cannabinoid receptor was cloned from rat and human cDNA libraries. The cDNA thus obtained when injected in CHO-$K_1$ cells led to the expression of the cannabinoid G-protein coupled receptor. (L. A. Matsuda, et al., "Structure of a Cannabinoid Receptor and Functional Expression of the Cloned cDNA", *Nature*, 346:561–564 (1990); C. Gerard et al., "Nucleotide Sequence of Human Cannabinoid Receptor cDNA", *Nucleic Acids Res.*, 18:7142 (1990)). Furthermore, the human cannabinoid receptor gene was shown to be localized to chromosome 6q14–q15. (M. R. Hoehe et al., "Genetics and Physics Mapping of the Human Cannabinoid Receptor Gene to Chromosome 6q14–q15" *New Biologist*, 3:880–885 (1991)). However, attempts to date to develop affinity labels of probes for the cannabinoid receptor have typically been unsuccessful. Therefore, a need exists to develop compositions which have a good binding affinity for the cannabinoid receptor and thus, can be used as cannabinoid receptor probes.

SUMMARY OF THE INVENTION

The present invention relates to a composition of matter, comprising a cannabinol compound having the following structural formula:

A composition of matter, comprising a cannabinol compound having the following structure

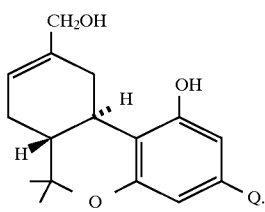

wherein:
Q is —$C(R^1)(Y^1)$—$(CH_2)_n$—$Z^1$ and $R^1$ is —H or —$CH_3$. In addition, $Y^1$ is —$CH_3$ or $Y^2$ and $Y^2$ is —$N_3$ or —NCS. Also, n is 4 or 6. Furthermore, $Z^1$ is —H, when $Y^1$ is $Y^2$, or is $Z^2$, when $Y^1$ is —$CH_3$, and $Z^2$ is —$N_3$ or —NCS.

DETAILED DESCRIPTION OF THE INVENTION

Figure 1:
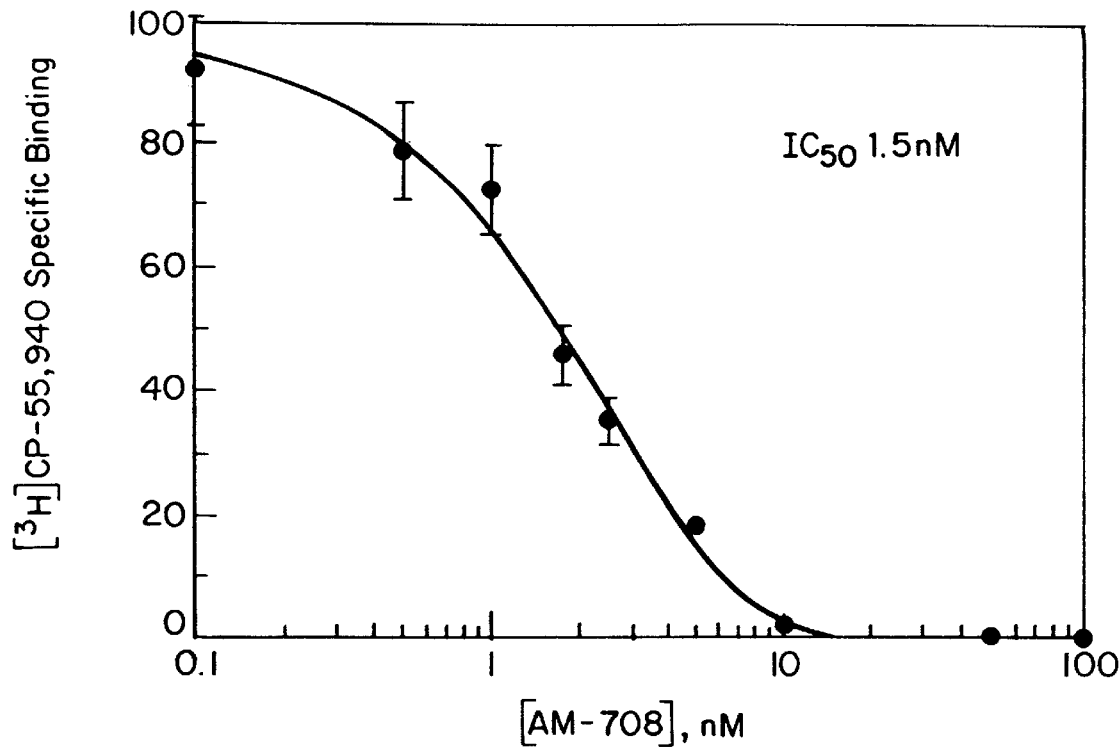
FIG. 1 is a plot of the binding affinity of the cannabinol compound (−)-11-OH-7'-NCS-1',1'-dimethylheptyl-$\Delta^8$-THC, for the cannabinoid receptor.

The features and other details of the invention, either as steps of the invention or as combinations of parts of the invention, will now be more particularly described and pointed out in the claims. It will be understood that the particular embodiments of the invention are shown by way of illustration and not as limitations of the invention. The principle features of this invention can be employed in various embodiments without departing from the scope of the invention.

The present invention relates a composition of matter which is useful as a cannabinoid receptor probe. A cannabinoid receptor probe, as defined herein, is a substance with a high affinity to bind to a cannabinoid receptor.

In one embodiment, the cannabinoid receptor probe comprises a composition having structural formula I. Structural formula I is as follows:

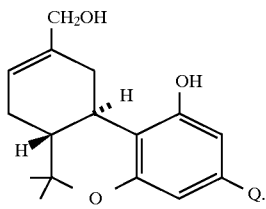

I

In this composition, Q is $CR^1Y^1$-$(CH_2)_n$-$Z^1$, where $R^1$ is —H or —$CH_3$, $Y^1$ is —$CH_3$ or $Y^2$, and $Y^2$ is —$N_3$ or —NCS. Furthermore, $Z^1$ is —H, when $Y^1$ is $Y^2$, or $Z^1$ is $Z^2$, when $Y^1$ is —$CH_3$. $Z^2$ is —$N_3$ or —NCS. The value of n is 4 or 6.

In this synthetic scheme approximately 0.5 to 2 moles of 4-hydroxy-myrtenyl pivalate (#1) and approximately 1 mole of a 1',1'-dimethyl-1'-(3,5-dihydroxyphenyl) bromoalkane (#2), having structural formula II, are dissolved in a suitable solvent to form a reaction solution. Suitable solvents include, for example, dry methylene chloride. Formula II has the chemical structure:

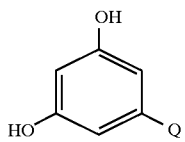

wherein Q is as defined for formula I. The synthesis of suitable 1',1'-dimethyl-1'-(3,5-dihydroxyphenyl) bromoalkanes is described in Example 9. The 4-hydroxymyrtenyl pivalate was also previously synthesized according to the known methods, specifically the method described in R. Mechoulam, ibid.

An excess of boron triflouride etherate is then added to the reaction solution, which is then blanketed with a suitable inert gas, such as nitrogen or argon. The reaction solution is then maintained at a temperature of appromixately –20° C. for about 3 hours. The reaction is subsequently quenched by suitable means, for example, washing the reaction mixture with an approximate 5% sodium bicarbonate solution. The organic layer is then separated and washed twice with water until it achieves an approximately neutral pH. The organic layer is then dried by known means, such as over sodium sulfate, to yield a 1',1'dimethylbromoalkyl-11-hydroxypivalate-$\Delta^8$-THC (#3). This compound is then purified by known means, such as by column chromatography.

Compound #3 is then mixed with lithium aluminum hydride, in a molar ratio of between about 1:1 to about 1:3, and an anhydrous solvent under conditions sufficient to react. Suitable conditions to react include stirring the solution for about 10 hours while maintaining the temperature at about 0° C. and under an inert gas, such as nitrogen or argon. Acceptable anhydrous solvents include tetrahydrofuran (THF).

The reaction is then stopped by acidifying the solution, for example, by adding 1N HCl. The solvent is subsequently evaporated from the solution and the residue is then extracted and purified by known means, yielding 11-hydroxy-1',1'-dimethylbromoalkyl-$\Delta^8$-THC (#4).

A 11-hydroxy-1',1'-dimethylazidoalkyl-$\Delta^8$-THC (#5) is then synthesized from compound #4 by mixing one mole of compound #4 with a dry solvent, such as dry chloroform, and then adding the compound #4 solution dropwise to about 1 to 3 moles of tetramethylguanidinium azide (TMGA), also in a solution of said dry solvent, while at approximately 0° C. and under an inert gas. The resultant mixture is then refluxed for approximately 6 to 12 hours. The solvent is subsequently evaporated from the solution and the residue is then extracted and purified by known means, thereby yielding compound #5.

In another embodiment, compound #5 is mixed with an excess of carbon disulfide and with an anhydrous solvent, such as anhydrous THF, to form a reaction mixture. The reaction mixture is stirred at room temperature while adding about 1 to 2 moles of triphenylphosphine per mole of compound #5 contained in the reaction mixture. After a suitable period, the solvent is subsequently evaporated from the solution and the residue is then extracted and purified by known means, thereby yielding 11-hydroxy-1',1'-dimethylalkylisothiocyanate-$\Delta^8$-THC (#6).

In an alternate embodiment, the cannabinoid receptor probe comprises a composition having structural formula III. Structural formula III is as follows:

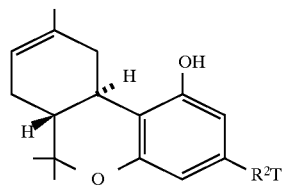

In this composition, $R^2$ is a pentyl or heptyl group while T is $-N_3$ or $-NCS$.

In this synthesis, a (3,5-dihydroxyphenyl) bromoalkane compound (#7) is refluxed for about 4 hours at approximately 90° C. in benzene with an excess of p-toluenesulfonic acid, thereby coupling the (3,5-dihydroxyphenyl) bromoalkane compound with (+)-cis/trans-p-mentha-2,8-dien-1-ol to give a bromoalkyl-$\Delta^8$-THC (#8). Examples of suitable (3,5-dihydroxyphenyl) bromoalkane compounds include 5'-bromo olivetol, whose synthesis is described in Example 7, or 1',1'-dimethyl-1'-(3,5-dihydroxyphenyl) bromoalkanes, described in Example 9. The (+)-cis/trans-p-mentha-2,8-dien-1-ol was obtained from Firmenich Inc., Princeton, N.J.

A solution of bromoalkyl-$\Delta^8$-THC (#8), in a solvent such as methylene chloride, is added dropwise to a solution with a concentration of about 1 to 3 moles of tetramethylguanidinium azide per mole of bromoalkyl-$\Delta^8$-THC, which is in the same type solvent as that of compound #8, and is maintained at about 0° C. The resulting mixture is then refluxed for about 8 hours and after which the solvent is evaporated from the solution and the residue is subsequently extracted and purified by known means, thereby yielding an azidoalkyl-$\Delta^8$-THC (#9).

In yet another embodiment, an azidoalkyl-$\Delta^8$-THC (#9) is mixed with an excess of carbon disulfide and with an anhydrous solvent, such as anhydrous THF, to form a reaction mixture. The reaction mixture is stirred at room temperature while adding about 1 to 2 moles of triphenylphosphine per mole of the azidoalkyl-$\Delta^8$-THC in the reaction mixture. After a suitable period, the solvent is subsequently evaporated from the solution and the residue is then extracted and purified by known means, thereby yielding an 11-hydroxyalkylisothio-cyanate-$\Delta^8$-THC is described in Examples 5 and 6.

The invention will now be further and specifically described by the following examples.

EXEMPLIFICATION

Example 1—Synthesis of 7'-Bromo-1',1'-dimethylheptyl-11-hydroxy privalate-$\Delta^8$THC 1.42 g (5.63 mmol) of 4-hydroxy-myrtenyl pivalate and 1.78 mg (5.63 mmol) of 1,1-dihydroxyl-7'-bromo-1',1'-dimethylheptyl-benzene (also named 1',1'-dimethyl-1'-(3,5-dihydroxyphenyl)-7'-bromo-heptane) were dissolved in 100 mL of dry methylene chloride. Boron triflouride etherate (4 mL, 32.5 mmol) was added to the solution under nitrogen at –20° C. After 3 hours, the reaction was quenched by washing the reaction mixture with 5% sodium bicarbonate solution. The organic layer was separated and washed twice with water until neutral, and then dried over sodium sulfate. After removal of the solvent, 2.56 g of a yellow oil was obtained. The crude compound was purified by column chromatography using 60% methylene chloride in petroleum ether as eluent. After purification, 1.61 g of 6 was obtained, the yield was 52.1%. $[\alpha]_D$-141.97° (CHCl$_3$); $^1$H NMR (CDCl$_3$) shifts observed were 6.37-6.23(dd,2H), 5.74 (d,1H), 5.08(s,1H), 4.49(s,2H), 3.36(t,2H), 2.66(m,1H), 2.22(m,1H), 1.38(s,3H), 1.21(s,9H), 1.19(s,6H), 1.1 (s,3H); Anal. (C$_{30}$H$_{45}$BrO$_4$) C,H.

Example 2—Synthesis of 11-hydroxy-7'Br-1',1'-dimethylheptyl-$\Delta^8$-THC

To a stirred solution of 6 (500 mg, 0.91 mmol) in 50 mL of andhydrous THF was added lithium aluminium hydride (52 mg, 1.37 mmol) at 0° C. under nitrogen. The mixture was then stirred at the same temperature for 10 hrs. The reaction was stopped by adding 1N HCl to make the solution acidic. THF was evaporated under vacuum. The residue was poured into water and was extracted with 3 portions of ethyl ether, the ether layer was then washed with saturated NaCl solution until neutral, and then dried over sodium sulfate. After removal of the ether, 460 mg of crude compound was obtained. It was purified by column (70% ethyl ether in petroleum ether as eluent). 361.7 mg of 3 was obtained, the yield was 85.5%. [$\alpha$]$_D$-152.42° C. (CHCl$_3$); $^1$H NMR (CDCl$_3$) shifts observed were 6.38-6.23 (dd,2H), 5.74(d, 1H), 4.99(s,1H), 4.07(s,2H), 3.44 (m,1H), 3.41-3.34 (t,2H), 1.40(s,3H), 1.21(s,6H), 1.12 (s,3H); Anal. (C$_{25}$H$_{37}$BrO$_3$) C,H.

Example 3—Synthesis of 11-hydroxy-7'-azido-1',1'-dimethylheptyl-$\Delta^8$-THC

A solution of 11-hydroxy-7'-bromo-1',1'-dimethylheptyl-$\Delta^8$-THC (138.2 mg, 0.297 mmol), in 10 mL of dry chloroform, was added dropwise to a solution of TMGA (94 mg, 0.594 mmol) in 5 mL of dry-chloroform at 0° C. under nitrogen. The resulting mixture was allowed to reach room temperature and then was refluxed overnight. The solvent was removed under a flow of nitrogen and then ethyl ether was added until no more precipitate formed. The precipitate was filtered out and was dried over sodium sulfate. After removal of the solvent, 124.8 mg of crude product was obtained and purified by column chromatography (70% ethyl ether in petroleum ether as eluent). 117.3 mg of compound (1) (light yellow oil) was obtained. The yield was 92.5%. [$\alpha$]$_D$-185.15° (CHCl$_3$); $^1$H NMR (CDCl$_3$) shifts observed were 7.01 (broad,1H), 6.33-6.25(d,2H), 5.73-5.71 (d,1H), 4.07-4.05(d,2H), 3.6-3.5(dd,1H), 3.25-3.18(t,2H), 2.67(m,1H), 1.35(s,3H), 1.18(s,6H), 0.98 (s,3H). Anal. (C$_{25}$H$_{37}$N$_3$O$_3$) C,H,N.

Example 4—Synthesis of 11-hydroxy-7'-isothiocyanate-1',1'-dimethylheptyl-$\Delta^8$-THC A solution of 11-hydroxy-7'-azido-1',1'-dimethylheptyl-$\Delta^8$-THC (100 mg, 0.23 mmol) and carbon disulfide (0.4 mL, 6.6 mmol) were mixed in 10 mL of anhydrous THF. The mixture was stirred at room temperature and then triphenylphosphine (92 mg, 0.35 mmol) was added. After 3 days, the solvent was evaporated under vacuum and the residue was purified by column chromatography (70% ethyl ether in petroleum ether as eluent). After purification 74.4 mg of compound (2) (white solid) was obtained. The yield was 73%. [$\alpha$]$_D$20.50°–152.64° $^1$H NMR (CDCl$_3$) shifts observed were 6.35-6.26(d,2H), 5.75-5.73(d,1H), 4.08(s,2H), 3.49-3.43(t,2H), 1.38(s,3H), 1.17(s,6H), 1.04(s,3H). Anal. (C$_{26}$H$_{37}$NO$_3$S) C,H,N.

Example 5—Synthesis of 1',1'-Dimethylpentyl-5'-isothiocyanate-$\Delta^8$-THC

The reagent 1',1'-Dimethylpentyl-5'-azido-$\Delta$-THC (170 mg, 0.44 mmol) in 10 mL of anhydrous THF and 1.0 mL of carbon disulfide (14.4 mmol) were mixed together. To the resulting mixture was added 245 mg of triphenyl phosphine (0.93 mmol). The mixture was stirred at room temperature for 3 days. The solvent was then evaporated. The crude compound was purified by column chromotography and produced 57.8 mg of compound 11. The yield was 33%. $^1$H NMR (CDCl$_3$) the shifts observed were 6.36-6.22(dd,2H), 5.41(d,1H), 5.06(s, broad, 1H), 3.42(t,2H), 3.24-3.14(dd, 1H), 2.69(dt,1H), 1.37(s,3H), 1.21(s, 6H), 1.10(s,3H).

Example 6—Synthesis of 1',1'-Dimethylheptyl-7'-isothiocyanate-$\Delta^8$-THC

1',1-Dimethylpentyl-7'-azido-$\Delta$-THC (300 mg, 0.81 mmol) in 18 mL of anhydrous THF and 1.2 mL of carbon disulfide were mixed together. The 1',1-Dimethylpentyl-7'-azido-$\Delta$-THC was synthesized from 1',1'-dimethyl-1'-(3,5-dihydroxyphenyl)-7'-bromo-heptane according to the method for synthesizing an azide described in Example 8. To the resultant solution was added 318 mg of triphenyl phosphine (1.22 mmol). The mixture was stirred at room temperature for 18 hours. The solvent was then evaporated. The crude compound was purified by column chromatography to produce 160.2 mg of compound 12. The yield was 51.1%. $^1$H NMR (CDCl$_3$) the shifts observed were 6.38-6.23(dd, 2H), 5.41(d,1H), 4.85(s,1H), 3.46(t,2H), 3.25-3.15(dd, 1H), 1.39(s,3H), 1.20(s, 6H), 1.11(s,3H).

Example 7—Synthesis of 5'-Bromo Olivetol

Triphenylphosphine and 4-phenoxybutyl bromide were refluxed in benzene for 36 hours to yield triphenyl(4-phenoxybutyl)phosphonium bromide in 81% yield.

The triphenyl(4-phenoxybutyl)phosphonium bromide was converted to an ylide using n-butyllithium and refluxing with 3,5-dimethoxybenzaldehyde in ether for 3 hours gave 1-(3,5-dimethoxyphenyl)-5-phenoxy-1-pentene as a 2:1 mixture of E:Z isomers. Purification was by column chromatography and gave a 60% yield. Subsequently, hydrogenation of 1-(3,5-dimethyoxypheny)-5-phenoxy-1-pentene over palladium on carbon (10%) under 50 psi of hydrogen gas resulted in the quantitative reduction of the pentene carbon-carbon double bond in to yield 1-(3,5-dimethoxyphenyl)-5-phenoxy-1-pentane. This phenoxy-1-pentane was then contacted with boron tribromide in benzene for 72 hours at 25° C. to deprotect the methoxy groups of the compound and substitute the phenoxy moiety with bromide to form 5'-bromo olivetol. After purification, an 80% yield was achieved.

Example 8—Synthesis of (−)5'-azido-$\Delta^8$-THC

The synthesis of (−)5'-azido-$\Delta^8$-THC was the same synthetic process as described for the composition of formula III. The 5'-bromo olivetol was refluxed for 4 hours in benzene and p-toluene-sulfonic acid to couple the olivetol compound with (+)-cis/trans-p-mentha-2,8-dien-1-ol and to form (−)-5'-Br-$\Delta^8$-THC. After purification, a yield of 50% was achieved. The (+)-cis/trans-p-mentha-2,8-dien-1-ol was obtained from Firmenich Inc., Princeton, N.J.

A solution of 500 mg (1.27 mmol) of (−)-5'-Br-$\Delta^8$-THC in 5 mL of methylene chloride was then added dropwise to a solution of 287 mg (1.82 mmol) tetramethylguanidinium azide in 5 mL of methylene chloride at 0° C. The reaction mixture was refluxed for 8 hours and the solvent was removed using a stream of nitrogen. The residue was extracted with ethyl ether. The extract was then purified by column chromatography using silica gel and ethyl ether/petroleum ether (1:5) as an eluent to produce 368 mg of a colorless gum. The yield of product was 81%. $^1$H NMR (CDCl$_3$) shifts observed were 6.26 (s,1H), 6.1 (s,1H), 5.42 (s,$_1$H), 3.12–3.28(m,3H), 2.7(dt,1H), 2.42 (t,2H), 1.7(s,3H), 1.37(s,3H), 1.1(s,3H).

Example 9—Synthesis of 1',1'-dimethyl-1'-(3,5-dihydroxyphenyl)-7'-bromo-heptane

The Grignard reagent, BrMg(CH$_2$)$_6$OTh, was synthesized by reacting TsCl, in pyridine at 0° C., with 6-bromo-1-hexanol to form Br(CH$_2$)$_6$Ts, which was subsequently reacted with sodium phenoxide, in DMF, to form 6-bromo-1-phenoxy hexane. The 6-bromo-1-phenoxy hexane was then reacted with magnesium, in anhydrous ether, to form said Grignard reagent.

The intermediary compound 1',1'-dimethyl-1'-(3,5-dihydroxyphenyl)-7'-bromo-heptane, used in the synthesis in Example 1, was formed by first reacting the Grignard reagent $BrMg(CH_2)_6OTh$ with 3,5-dimethylacetylphenol in anhydrous ether at 34° C. The resulting product was then demethylated by successive reactions first with gaseous HCl and then with trimethylaluminum, in toluene, at 100° C. After demethylation, the product was brominated by reaction with boron tribromide, in benzene, at room temperature. In this synthetic process of forming the Grignard reagent and also forming 1',1'-dimethyl-1'-(3,5-dihydroxyphenyl)-7'-bromo-heptane, all reactions were conducted with approximately equal portions of reagents (i.e., a 1:1 molar ratio).

Other 1'-(3–5 dihydroxyphenyl) bromoalkanes have been synthesized through the use of different Grignard reagents or by substituting 3,5-dimethoxybenzylaldehyde in the synthesis for 3,5-dimethylacetylphenol. For example, substitution of $BrMg(CH_2)_6OTh$ with $BrMg(CH_2)_4OTh$ produced a 5'-bromo-pentane instead of said 7'-bromo-heptane. $BrMg(CH_2)_4OTh$ was synthesized by the method for forming $BrMg(CH_2)_6OTh$. In addition, use of 3,5 dimethoxybenzyl aldehyde, without the subsequent reaction with HCl and $Al(CH_3)_3$, will produce 1'-bromoaldehyde in lieu of 5'- or 7'-bromoalkane.

Furthermore, the use of the commerically available Grignard reagent butylMgBr with 3,5-dimethoxybenzyl aldehyde, without a subsequent reaction with HCl and $Al(CH_3)_3$, will form 1'-(3,5-dihydroxyphenyl)-1'bromo-pentane.

Cannabimimetic Activity Evaluation

5'-azido-THC was evaluated in vivo and compared to the parent compound (−)-$\Delta^8$-THC for cannabimimetic activity. Both analogs were tested in male ICR (Institute of Cancer Research) mice (Harlan, Frederick, Md.) following intravenous injection, for their abilities to produce sedation (decreased locomotor activity) and catalepsy (induction of ring immobility) as measures of drug-induced behavioral effects. They were also evaluated in the same mice for their abilities to produce hypothermia and antinociceptive activity in the mouse tail-flick assay.

The results obtained are shown in Table I. Dose-response data were analyzed statistically by ANOVA, and the potency ($ED_{50}$ value) and efficacy (maximum effect) were determined. The maximum effects given represent percent inhibition (of locomotor activity), ° C. (of hypothermia), percent immobility (of catalepsy) and percent MPE (maximum possible effect of latency of antiociception procedure). The data indicate that 5'-azido-THC is 6.5 times (catalepsy) and 19 times (hypothermia) more potent (on a milligram/kilogram basis) than the parent compound in these pharmacological tests.

This evaluation was performed by methods described in M. D. Compton et al., *J. Med. Chem.*, 34:3310 (1991), A. Makriyannis et al., *Life Sci.*, 47:2173 (1990), and A. Charalandous et al., *Pharmacol. Biochem. Behav.*, 40:509 (1991).

TABLE I

| Analog | Locomotion Inhibition | Hypothermia (Δtemperature) |
|---|---|---|
| (−)-$\Delta^8$-THC | 1.9 [1.3–2.9] | 15.5 [6.1–3.9) |

TABLE I-continued

| | (79%) | (−5.9° C.) |
|---|---|---|
| (−)-5'-$N_3$-$\Delta$-THC | 0.2 [0.11–0.23] (73%) | 0.8 [0.3–2.6] (−3.8° C.) |

| Analog | Catalepsy Immobility | Antinociception MPE |
|---|---|---|
| (−)-$\Delta^8$-THC | 5.2 [3.6–7.7] (58%) | 1.5 [0.6–4.1] (100%) |
| (−)-5'-$N_3$-$\Delta$-THC | 0.8 [0.4–1.6] (57%) | 0.1 [0.03–0.47] (100%) |

Receptor Binding Assay

The affinity of compositions of this invention for cannabinoid binding sites was tested by using membrane preparations from rat forebrains. A composition is tested by incubating various concentrations of the composition with approximately 50 μg of rat forebrain membrane, 20 mM Tris Buffer, 3 mM $MgCl_2$, 1 mM EDTA (pH, 7.4) containing 0.1% bovine serum albumin, and 0.8 nM of the cannabinoid radioligand [$^3$H]CP-55,940, (Dupont-NEN). Assays were incubated in Regisil-treated test tubes for 1 hour at 30° C. and were subsequently filtered on GF/C filters using a Brandell M-24 Cell Harvester. Following four washes with 20 mM Tris buffer (pH 7.4) and 3 mM $MgCl_2$, the GF/C filters were collected, and shaken for 1 hour with 2 mL of 0.1% SDS. Ligand binding was counted on a Beckman liquid scintillation counter.

Non-specific binding was assessed from tubes containing 250 nM desacetyllevo-nantradol by the method described in W. A. Devane et al., *Determination and Characterization of a Cannabinoid Receptor in Rat Brain*, Mol. Pharmacol., 34:605 (1988). Data were collected from 3 experiments performed on 11-hydroxy-7'-azido-1',1'-dimethylheptyl-$\Delta^8$-THC and on 11-hydroxy-7'-isothiocyanate-1',1'-dimethyl-heptyl-$\Delta^8$-THC, each. $IC_{50}$ values, were calculated by non-linear regression analysis using Quatro Pro, are provided in Table I.

An alternate affinity test used approximately 30 μg of rat forebrain membrane in a buffer containing 20 mM potassium diethyl malonate (pH 7.4), 3 mM $MgCl_2$, 0.01% β-cyclodextrin, and 100 fmol/mL [$^3$H]CP-55,940, (Dupont-NEN). The assays were incubated in Regisil-treated test tubes for 1 hour at 30° C. and were subsequently filtered on GF/C filters. Just prior to filtration, 200 μL of 50 mg/mL bovine serum albumin is added. Following filtration, ligand binding was counted on a Beckman liquid scintillation counter.

Non-specific binding was assessed from tubes containing 100 nM desacetyllevo-nantradol by the method described in W. A. Devane et al., *Determination and Characterization of a Cannabinoid Receptor in Rat Brain*, Mol. Pharmacol., 34:605 (1988). Data were collected from 3–5 experiments performed on (−)5'-azido-$\Delta^8$-THC and as compared to the affinity demonstrated by $^8$-THC. $IC_{50}$ values are provided in Table II.

TABLE II

| Composition | $IC_{50}$ (nM) |
|---|---|
| 11-hydroxy-7'-azido-1',1'-dimethylheptyl-$\Delta^8$-THC | 2.5 |
| 11-hydroxy-7'-isothiocyanate-1', | 1.5 |

TABLE II-continued

| Composition | IC$_{50}$ (nM) |
| --- | --- |
| 1'-dimethylheptyl-$\Delta^8$-THC (-)5'-azido-$\Delta^8$-THC | 31 |
| $^8$-THC | 75 |

Figure 2:
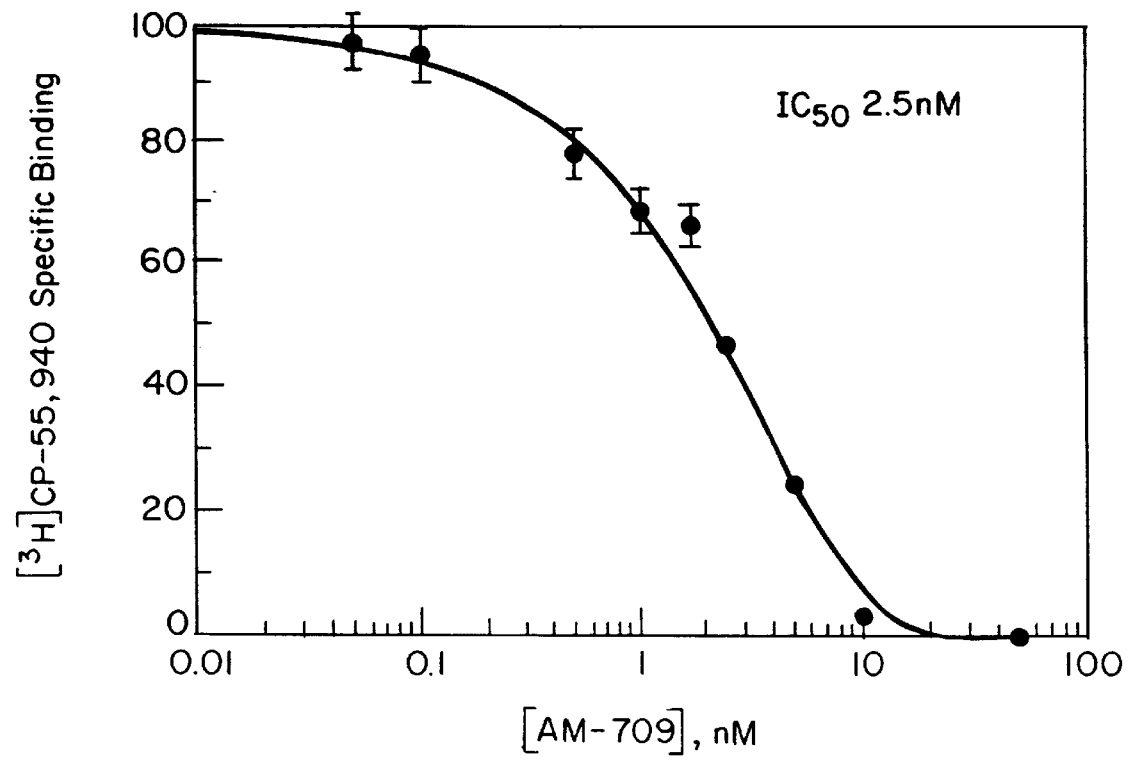
FIG. 2 is a plot of the binding affinity of the cannabinol compound (−)-11-OH-7'-$N_3$-1',1'-dimethylheptyl-$\Delta^8$-THC, for the cannabinoid receptor.
Figure 3:
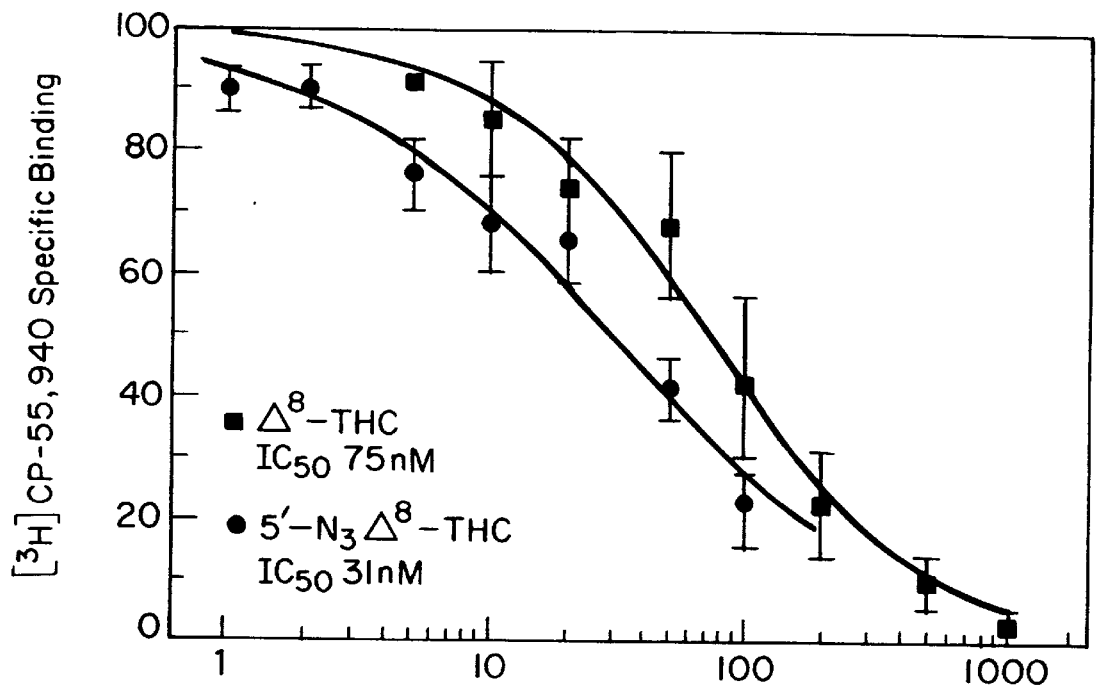
FIG. 3 is a plot of the binding affinity of the cannabinol compounds (−)-5'-$N_3$-$\Delta^8$-THC, as compared with (−)-$\Delta^8$-THC.

The data from these receptor binding assays is provided in FIGS. 1 to 3.

Receptor Inactivation Tests

Figure 4:
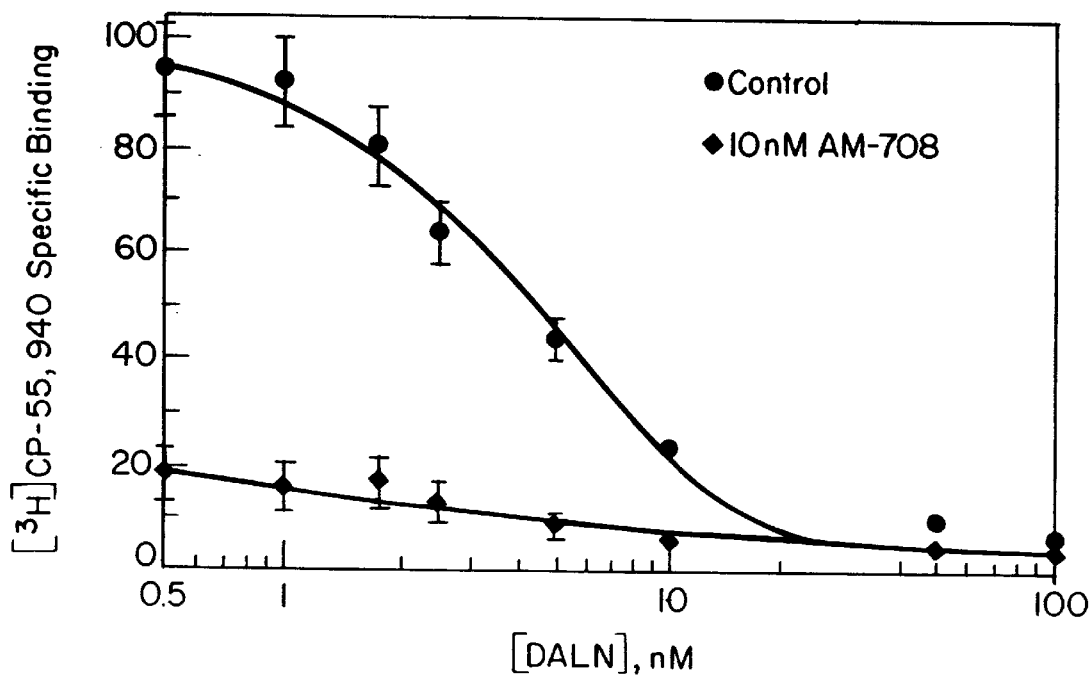
FIG. 4 is a plot of the effect of equilibration of a 11-OH-7'-NCS-1',1'-dimethylheptyl-$\Delta$-THC on cannabinoid receptors binding inhibitor.
Figure 5:
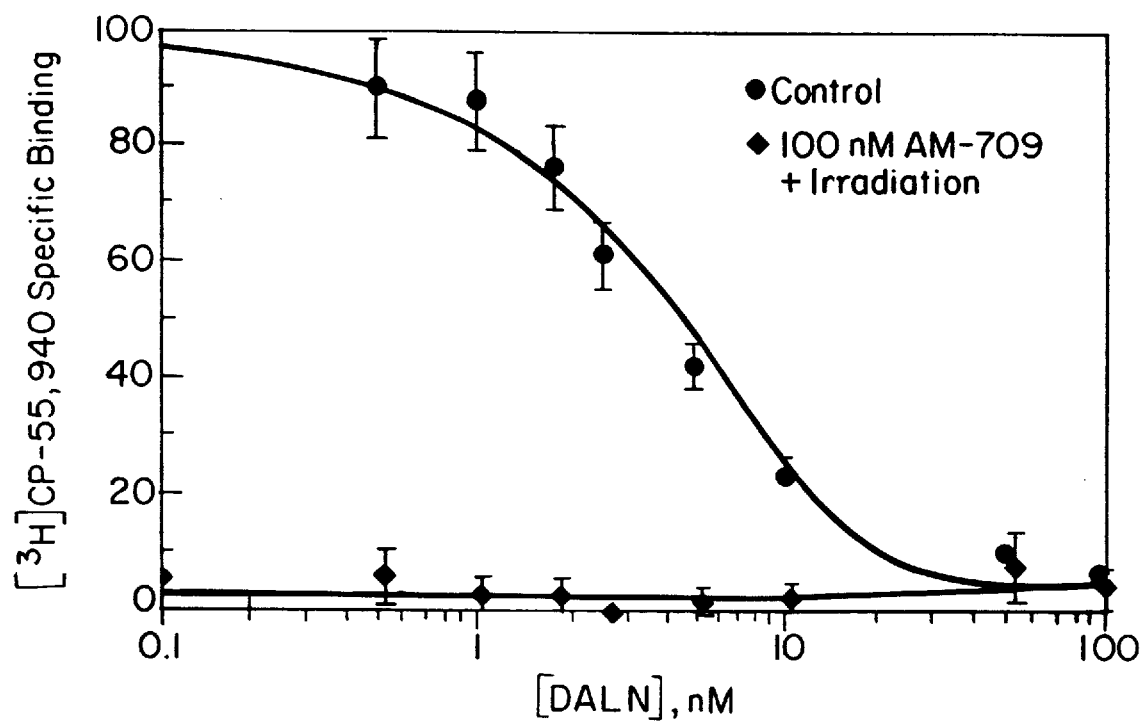
FIG. 5 is a plot of photo irradiation test data of cannabinoid receptor binding inhibition resulting from 11-OH-7'-$N_3$-1',1'-dimethylheptyl-$\Delta^8$-THC.

The ability of affinity ligands to inactivate the cannabinoid receptor in vitro was tested through photoirradiation experiments. All procedures involving affinity ligands were conducted in the dark using only a safety light. Rat forebrain membranes (1–3 mg) in 20 mM Tris Buffer, 3 mM MgCl$_2$, and 1 mM EDTA (pH 7.4) were incubated with an appropriate amount of either 11-hydroxy-7'-azido-1',1'-dimethylheptyl-$\Delta^8$-THC or 11-hydroxy-7'-isothiocyanate-1',1'-dimethyl-heptyl-$\Delta^8$-THC, in a six-well culture plate for 1 hour at 30° C. At the end of the equilibration membranes incubated with 11-hydroxy-7'-azido-1',1'-dimethylheptyl-$\Delta^8$-THC were placed on ice and irradiated for 13 minutes with UV light. Membranes incubated with either of the two compounds were then pelleted using a bench top microcentrifuge. The pellets were subsequently washed at least three times with the working buffer containing 1 mg/mL bovine serum albumin, allowing at least 10 minutes between each wash for equilibration. The final pellets were resuspended in the working buffer and assayed for cannabinoid binding activity by the method of Devane et al., referenced above. The test results are shown in FIGS. 4–5.

In an alternate receptor inactivation test, 0.5–3 mg of rat forebrain membrane was incubated with (–)5'-azido-$\Delta^8$-THC, previously resuspended in 5% β-cyclodextrin in 12-well tissue culture plates containing 1 mL of 20 mM potassium diethyl malonate (pH 7.4) and 0.01% β-cyclodextrin. The assay was incubated for 1 hour at 30° C. and then was placed on ice and irradiated for 13 minutes with shortwave UV light from a UVGL-25 mineralight at 10 cm distance for 20 minutes.

In the 5'-azido-$\Delta^8$-THC equibrated and irradiated membranes, no specific receptor binding was observed. Thus, the compound did not irreversibly inactivate the receptors.

However, the high affinity of the 7'-azido and 7'isothiocyanate of 11-OH-1',1'-dimethyl heptyl-$\Delta^8$-THC compounds for the cannabinoid receptor has been demonstrated by their IC$_{50}$ values, the concentration required for half-maximal inhibition. The ability of these compounds to completely inactivate the cannabinoid receptor has also been demonstrated in vitro.

Instrumentation

Optical rotations were determined on a Perkin-Elmer 241 polarimeter in chloroform. NMR spectra were recorded on a Bruker WP-200sy (200 MHz) spectrometer using tetramethylsilane as an internal reference. Analytical thin-layer chromatography were performed with E. Merck DC-Plastikfolien Kieselegel 60 F254. Column chromatography was performed with E. Merck silica gel 60 (230–400 mesh). The elementary analyses were performed by the analytical services of Baron Consulting Co. on a Finigan 4500 GC/MS spectrometer using a direct exposure probe and ammonia as the carrier gas.

Equivalents

Those skilled in the art will recognize, or be able to ascertain, using no more than routine experimentation, many equivalents to specific embodiments of the invention described specifically herein. Such equivalents are intended to be encompassed in the scope of the following claims.

What is claimed is:

1. A compound represented by the following structural formula:

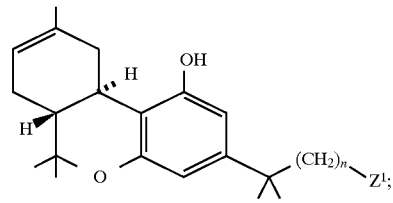

wherein:

n is an integer from three through seven; and

Z$^1$ is —N$_3$ or —NCS.

2. A compound represented by the following structural formula:

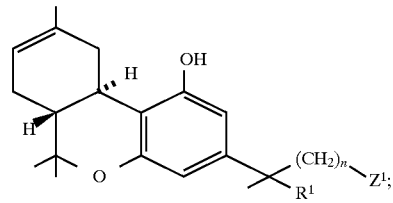

wherein:

R$^1$ is —H or —CH$_3$;

n is an integer from three through seven; and

Z$^1$ is —N$_3$ or —NCS.

3. The compound of claim 1 wherein the compound is 1',1'-dimethylheptyl-7'-isothiocyanate-$\Delta^8$-THC.

4. The compound of claim 1 wherein the compound is 1',1'-dimethylpentyl-7'-isothiocyanate-$\Delta^8$-THC.

* * * * *